United States Patent [19]

Altschuler

[11] Patent Number: 5,318,547
[45] Date of Patent: Jun. 7, 1994

[54] SHEATHED HYPODERMIC NEEDLE

[76] Inventor: Bruce R. Altschuler, 4542 English Ave., Ft. Meade, Md. 20755

[21] Appl. No.: 821,728

[22] Filed: Jan. 15, 1992

[51] Int. Cl.⁵ .......................................... A61M 5/32
[52] U.S. Cl. .................................. 604/198; 604/263
[58] Field of Search .............. 604/263, 198, 192, 187, 604/110, 164

[56] References Cited

U.S. PATENT DOCUMENTS

| | | | |
|---|---|---|---|
| 4,573,976 | 3/1986 | Sampson et al. | 604/263 X |
| 4,631,057 | 12/1986 | Mitchell | 604/198 |
| 4,655,751 | 4/1987 | Harbaugh | 604/198 |
| 4,664,653 | 5/1987 | Sagstetter et al. | 604/197 |
| 4,737,144 | 4/1988 | Choksi | 604/198 |
| 4,738,663 | 4/1988 | Bogan | 604/198 |
| 4,846,809 | 7/1989 | Sims | 604/198 |
| 4,908,023 | 3/1990 | Yuen | 604/118 |
| 4,923,446 | 5/1990 | Page et al. | 604/198 |
| 4,923,447 | 5/1990 | Morgan | 604/198 |
| 4,935,016 | 6/1990 | Deleo | 604/198 |
| 4,947,863 | 8/1990 | Haber et al. | 128/764 |
| 4,957,490 | 9/1990 | Byrne et al. | 604/197 |
| 5,024,616 | 6/1991 | Ogle, II | 604/192 |
| 5,135,510 | 9/1992 | Maszkiewicz et al. | 64/198 X |
| 5,503,018 | 10/1991 | Talonn et al. | 604/198 |

Primary Examiner—John D. Yasko
Attorney, Agent, or Firm—Edward W. Nypaver; Donald J. Singer

[57] ABSTRACT

A sheathed syringe assembly including a syringe having a cylindrical body provided with a needle at one end thereof and a plunger slideably disposed within said cylindrical body for aspirating or dispensing substances into or from the cylindrical body. A sheath assembly comprised of inner and outer tubular members is attached to the cylindrical body. The inner tubular member is telescopically received in the outer member for reciprocal movement therein between a retracted position exposing said needle and an extended position covering said needle to prevent accidental needle stick. The sheath assembly is provided with a ratchet means for manually advancing said inner tubular member into the extended position with the same hand holding said syringe assembly.

8 Claims, 3 Drawing Sheets

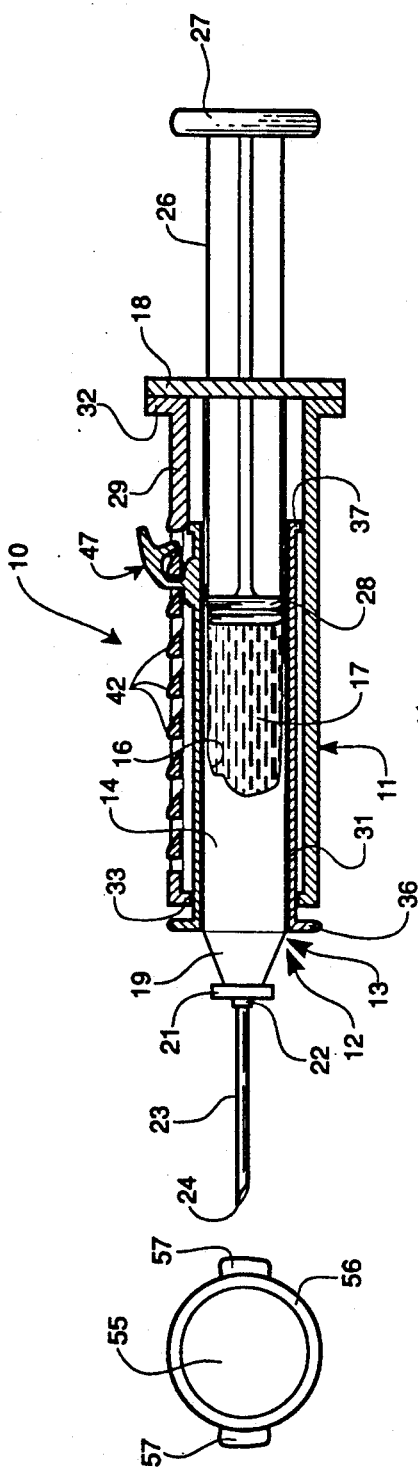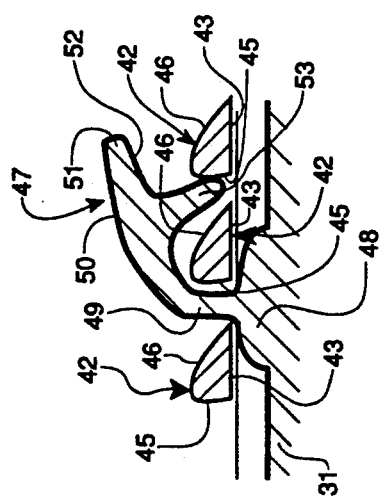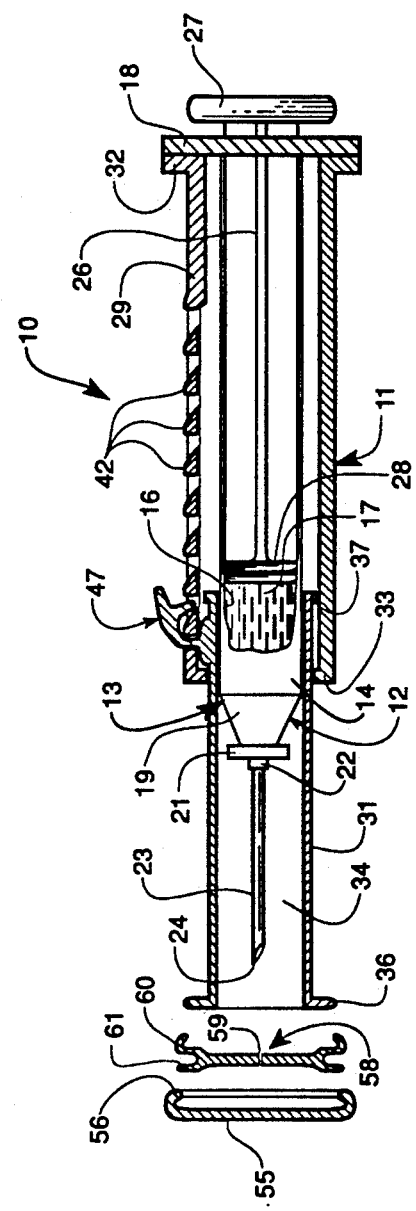

SHEATHED HYPODERMIC NEEDLE

RIGHTS OF THE GOVERNMENT

The invention described herein may be manufactured and used by or for the Government of the United States for all governmental purposes without the payment of any royalty.

BACKGROUND OF THE INVENTION

This invention relates to a protective sheath adapted to cover a syringe needle after use to preclude inadvertent needle stick puncture wounds.

Hypodermic needles are frequently used to administer medications and anaesthetics to patients or withdraw body fluids therefrom by health care personnel. Conventional hypodermic syringes comprise a cylindrical tube with a flange or laterally projecting finger tabs at one end adapted to be supported by the fingers of the user and an extended construction at the other end provided with a suitable mounting for releasably coupling a hypodermic needle thereto. The end of the tube having the flange is open for receiving a plunger used to draw fluid into the tube or dispense it through the needle. The syringes can be disposable, generally formed of plastic, or reusable and formed of a suitable metal which is sterilizable. Disposable syringes generally are supplied in a peel-a-way blister package with needles obtained separately and also contained in peel-a-way blister packages.

Typically, the needles are supplied with protective caps or sheaths which snugly encapsulate the needle. Once the cap is removed, the needle is exposed and poses the risk of accidental puncture to the user and other health care attendants due to incidental handling or mishandling by such users or attendants. Replacing the cap after usage requires aligning the cap with the needle and telescopically sliding the cap thereon. This procedure requires two hands and the undivided attention of the user in a motionless environment. The chance of accidental finger puncture is greatly enhanced during recapping of a used needle and can be extremely hazardous when the needle was used on an infected patient having a blood borne disease. Recent infection control guidelines discourage the recapping of used needles due to the danger to the other hand holding the cap when approaching the distal or pointed end of the needle. When not recapped, the used, exposed needle becomes a temporary hazard to the health care provider during surgical and dental procedures and routine patient care. For example, syringes with exposed needles are sometimes handed over from one nurse to another and needle destroying apparatus may not be readily convenient.

In light of the hazards posed by dangerously contaminated, exposed syringe needles, many attempts have been made to sheath or otherwise cover such used needles to reduce the hazards of accidental needle stick. While such known sheathed syringes have served the purposes for which they were intended, they have not been entirely satisfactory for several reasons. For example, certain ones of these prior known devices do not positively retain or lock the sheath in the extended needle protective position. Others include a complicated design of many parts making the devices relatively expensive and difficult to manufacture. As far as can be ascertained, all known sheathed syringe assemblies require the user to employ both hands to extend the sheath into the extended, needle protective position.

SUMMARY OF THE INVENTION

Accordingly, it is a primary object of the present invention to avoid the above noted disadvantages by providing a hypodermic syringe having an improved protective sheath assembly.

It is another object of this invention to provide the foregoing sheathed hypodermic syringe with novel actuating means to facilitate smooth and easy extension of the protective sheath over and past the needle point.

It is still another object of the present invention to manually extend the foregoing protective sheath expediently with the same hand holding the syringe.

It is a further object of this invention to provide an improved protective sheath assembly releasably attachable to existing syringes.

It is still a further object of the present invention to provide a hypodermic syringe with an improved protective sheath assembly which is simple and strong in construction, durable and rugged in use, expedient and reliable in operation, and low in cost.

The sheathed hypodermic syringe of this invention is characterized by the provision of a sheath assembly comprised of inner and outer tubular members. The inner member is telescopically received in the outer member and slidable relative thereto for extension about the syringe needle to preclude accidental needle stick. The sheath assembly is provided with a ratchet arrangement for manual actuation by the same hand holding the syringe assembly at the safe end of the syringe remote from the needle.

The foregoing and other objects, advantages, and characterizing features of the present invention will become clearly apparent from the ensuing detailed description thereof considered in conjunction with the accompanying drawings wherein like reference numerals denote like parts throughout the various views.

BRIEF DESCRIPTION OF THE DRAWING FIGURES

FIG. 3 is a longitudinal sectional view, showing the inner sheath member in its retracted position;

FIG. 4 is a view similar to FIG. 3, showing the inner sheath member in its extended position and a cap adapted to be snap-fitted over the open end of the inner sheath member;

FIG. 5 is an enlarged, fragmentary, sectional view, illustrating the pawl and teeth of the ratchet arrangement;

DESCRIPTION OF AN ILLUSTRATIVE EMBODIMENT

Figure 1:
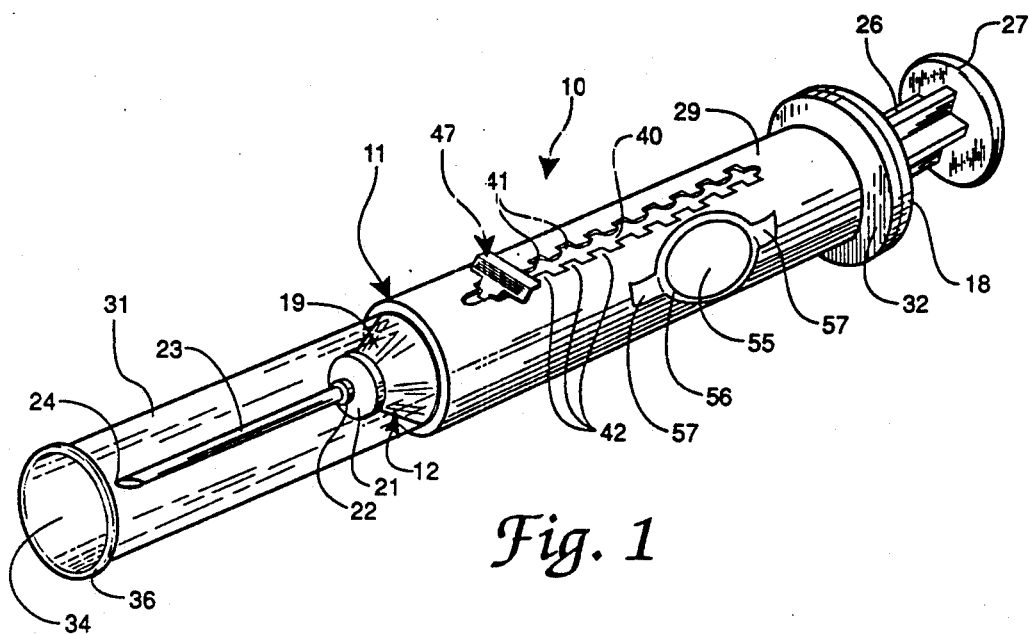
FIG. 1 is a perspective view of a sheathed hypodermic syringe constructed in accordance with the present invention, showing the inner sheath member in its extended position.
Figure 2:
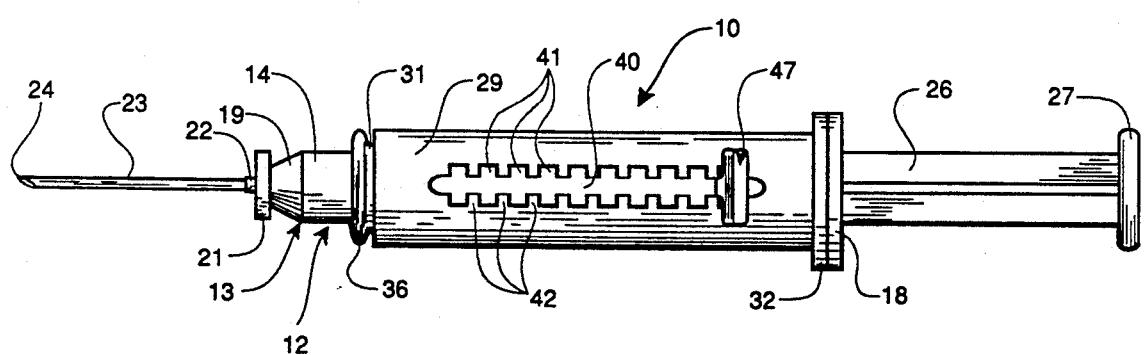
FIG. 2 is a top plan view, showing the inner sheath member in its retracted position.

Referring now in detail to the drawings, there is shown in FIG. 1 an illustrative embodiment of a sheathed hypodermic syringe constructed in accordance with this invention and comprehensively designated 10, comprising a sheath assembly, generally designated 11, and a syringe and needle assembly, generally designated 12. The syringe and needle assembly 12 can be of any conventional type which is currently used in the health care industry. The assembly 12 comprises a syringe 13 having a cylindrical body 14 defining a chamber 16 (FIGS. 3 and 4) for containing a substance 17 to be injected and terminates at one end in a flange 18 adapted to be supported by the fingers of a user. The body 14 can be formed of a transparent plastic with graduation indicia (not shown) imprinted thereon, if desired, to determine the amount of substance to be aspirated into the body 14 or dispensed therefrom.

The other end of body 14 terminates in a conical end portion 19 provided with an adapter 21 having a mounting member 22 for receiving an elongated, hollow needle 23 attached thereto. The needle 23 is coaxially arranged within the body 14 in communication with chamber 16 and terminates in a sharp point 24 at the distal end of the needle. The end of the body 14 having the flange 18 is open for receiving an axially extending plunger 26 of generally cruciform configuration in cross section and which is moved linearly within chamber 16 by a generally flat, manually graspable handle 27 rigidly secured to the outer end of plunger 26. The inner end of plunger 26 is provided with a piston 28 to effect aspirating or dispensing of the substance 17 into and from the chamber 16 through the passage of needle 23.

A significant feature of this invention resides in the provision of the sheath assembly 11 which can be an integral manufactured component of a new syringe or a separate component adapted to be retrofitted to existing stock syringes. The sheath assembly 11 comprises an outer tubular sheath member 29 and an inner tubular sheath member 31 telescopically received within member 29 for reciprocal sliding movement relative thereto between the retracted position shown in FIG. 3 and an extended position covering the needle 23 to prevent access thereto as shown in FIG. 4. The outer sheath member 29 is formed at one end thereof with a radially outwardly extending flange 32 rigidly fixed to the syringe flange 18. While the flanges 18 and 32 of the syringe assembly 12 and sheath assembly 11, respectively, are shown as being circular, it should be understood that such flanges can take any configuration desired within the purview of this invention. The other end of member 29 is provided with an inwardly extending formation serving as a shoulder or stop 33 for a purpose that will hereinafter become apparent.

The inner sheath member 31 is formed with an axial bore 34 for accommodating the syringe 13 and is mounted for axial reciprocal movement relative to the syringe 13 and outer sheath member 29. The inner or forward end of sheath member 31 is formed with an annular bead 36 for a purpose hereinafter explained. The rearward end of inner sheath member 31 is formed with a radially outwardly extending annular shoulder or stop 37 cooperable with shoulder 33 of outer sheath member 29 to prevent complete detachment of member 31, when extended, from within member 29.

Means in the form of a ratchet system is provided for manually advancing or retracting the inner sheath member 31 easily with the same hand used to hold the syringe and actuate the plunger 26. Such ratchet means includes an elongated slot 40 extending lengthwise of outer sheath member 29 and formed with a plurality of opposed lateral indentations 41 defining a plurality of opposed ratchet teeth 42. As best shown in FIG. 5, each tooth 42 includes a flat horizontally extending bottom surface 43 forming a part of the inner wall surface of outer sheath member 29, a generally flat vertical forward wall surface 45, and an upper cam surface 46 extending from the upper end of surface 45 and curving rearwardly and downwardly to the rearward end of bottom surface 43.

The terms upper, upwardly, vertical, lower, forward, rearward and the like as used herein are applied only for convenience of description with reference to FIGS. 3-5 and should not be taken as limiting the scope of this invention.

A pawl member 47 is provided with a base portion 48 welded or otherwise fixedly secured to the outer surface of inner sheath member 31 and is formed with an upwardly extending neck portion 49 having a width of slightly lesser dimension than the width of slot 40 for reciprocal movement therein. The neck portion 49 widens into a transition portion 50 having a width substantially straddling opposed indentations 41 above slot 40. The upper surface of transition portion 50 extends upwardly and rearwardly forming a lip 51, the bottom surface 52 of which merges with a detent 53 projecting downwardly and slightly rearwardly at a slight angle to a true vertical between adjacent teeth 42. While holding the sheathed syringe 10 with one hand, the user places his thumb or other finger of the same hand on pawl member 46 exerting a forward force thereon causing the detent 53 to ride along the cam surface 46 of successive teeth 42 to advance the inner sheath member 31 into an extended position covering the needle 23. Inadvertent reverse movement of inner sheath member 31 is prevented by detent 53 being engagable with the flat vertical surface 45 of the adjacent preceding or rearward tooth 42. In order to retract the inner shield member 31, the user exerts upward pressure with the thumbnail beneath lip 51 to free the inner sheath member 31 for reverse movement into the retracted position.

As shown in FIGS. 3 and 4, a cap 55 of slightly larger outside dimensions than inner sheath member 31, but of the same general circumferential configuration, is provided with an inturned lip or flange 56 adapted to be snap-fitted over bead 36 of the inner sheath member 31. This arrangement completely encapsulates the needle 23 precluding any possible needle stick injury to the user. The cap 55 can initially be provided with breakaway lateral tabs 57 adhesively attached to the outer sheath member 29 (FIG. 1) until required to cover the needle 23 and close the open end of the inner sheath member 31.

In use, the operator, i.e. health care provider, peels away the blister pak of the sheathed hypodermic syringe 10 exposing the same with the inner sheath member 31 retracted as shown in FIG. 3. Next, the operator peels away the blister pak from the capped needle and inserts the same into the mounting member 22 of syringe 13. In some instances, a composite package can include a fresh, sheathed syringe 13 already having a needle 23 inserted therein, as well as an ampule of medication provided in chamber 16. In any event, the needle is provided with a protective cap or cover which must be removed just prior to inserting the needle 23 into the skin or tissue of the patient. With one hand on the body of the patient, the plunger 26 is then depressed by the fingers of the other hand to expel the substance 17 through chamber 16 and needle 23 for injection in the usual way. Of course, an empty sheathed syringe 10 can be employed to withdraw blood or other body fluids from a patient. In either case, upon withdrawing the needle 23 from the patient with the user's one hand still placed on the patient's body and while holding the sheathed syringe with the other hand, the operator exerts forward pressure on the pawl 47 by the thumb of the same other hand to advance the inner sheath member 31 to its extended position past the needle point 24 for substantially covering the needle 23. This effectively locks the sheath member 31 in such extended position due to the prevention of reverse movement by the engagement of detent 53 with the substantially flat vertical surface 45 of the preceding tooth 42. The operator may then be required to hand the sheathed syringe 10 to an assistant or place it on a table. Inadvertent needle stick through multiple handling would be highly improbable, if not impossible, because of the relative small diameter opening of the sheath member 31 and the projection of the outer end of member 31 at least one-half inch beyond the needle point 24. However, as an added safety measure, the breakaway cap 55 can be detached from outer sheath member 29 and snap-fitted behind bead 36 of the member 31 for completely encapsulating the needle 23.

The above procedure was described in advancing the inner sheath member 31 to its fully extended position. In such procedures, only two ratchet settings, i.e. teeth adjacent the fully retracted and fully extended positions, would be required. The plurality of ratchet settings shown in the drawings can accommodate a variety of needle lengths so that with shorter needles the inner sheath member 31 would not have to be fully extended. However, the extent of inner sheath member extension would require reliance on the part of the operator to ensure complete coverage of the needle. Suitable markings or indicia can be provided on the outer sheath member 29 to indicate the range of needle lengths that could be safely employed with a particular sheath assembly.

In addition to cap 55, a thin, soft, flexible diaphragm 58 of generally similar outside dimensions as cap 55 can be employed to cover the open end of inner sheath member 31 under certain non-sterile field emergency situations, such as in field hospitals, ambulances, combat field kits or for rescue and aerovac operations. In order to prevent gross contamination of the needle 23, such as might occur with the ingress of sand and other particulates into sheath member 31 during emergency combat/disaster field conditions, particularly where the needle would be used more than once, the diaphragm 58 could be an integral manufactured part of a new syringe 10 having its inner sheath member 31 already disposed in the extended position. If desired, the diaphragm 58 could be formed with a precut slit 59 or other suitable aperture to facilitate passage of the needle 23 therethrough upon retraction of the inner sheath member 31 when readied for use. The diaphragm 58 is formed with an inturned flange or lip 60 adapted to be snap-fitted over sheath member bead 36 and an opposite out-turned flange or bead 61 for receiving the hard cap 55 at the end of the procedure without having to remove the diaphragm 58.

It should be understood that the entire sheathed hypodermic syringe assembly 10 can be formed of an inexpensive plastic material for immediate disposal after use or of metal, such as stainless steel or a suitable alloy, which can be sterilized for reuse. The sheath assembly 11 can be transparent or, if opaque, formed with windows to provide a visual assessment of the liquid contents within chamber 16.

Figure 6:
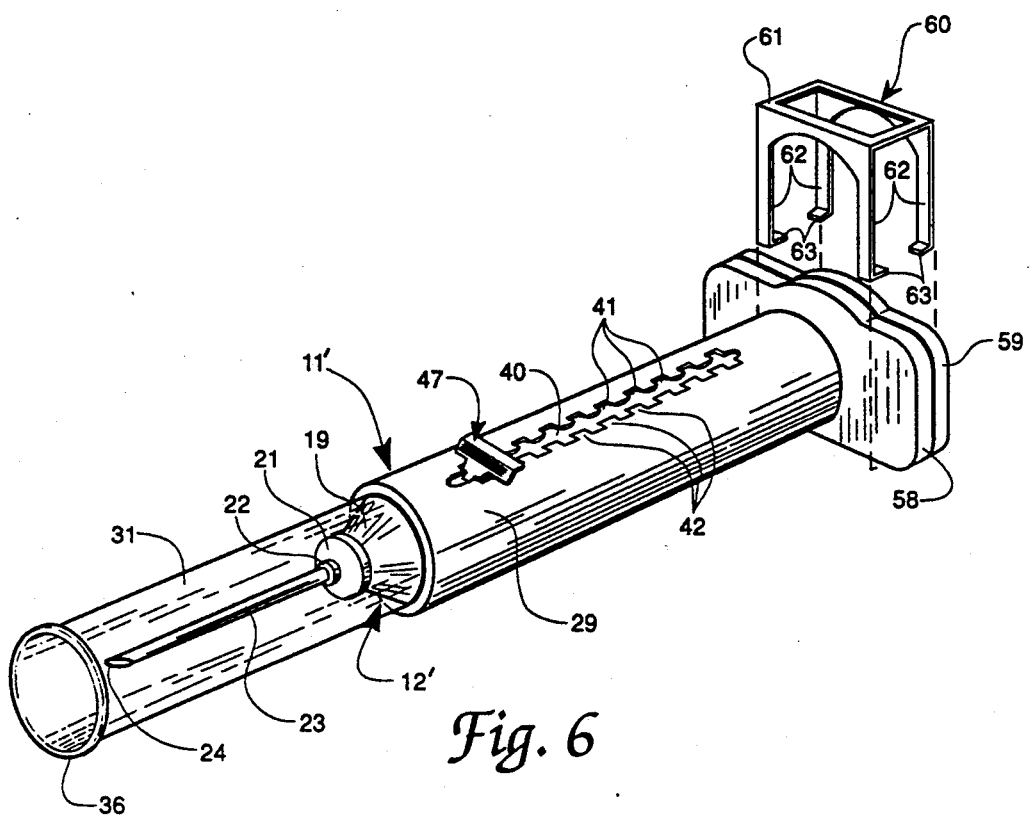
FIG. 6 is a perspective view of another embodiment of this invention, showing a clip for securing a separable sheath assembly to an existing syringe.

FIG. 6 illustrates a form of this invention in which the sheath assembly 11', per se, is separately stocked and retrofitted to conventional hypodermic syringes 12'. The separate sheath assembly 11' is identical in construction and operation to the sheath assembly 11 first described above except for a differently configurated flange 58 adapted to mate with the flange 59 of the syringe assembly 12'. It should be appreciated that the configurations of flanges 58 and 59 can vary widely and the specific shape thereof is in no way limited to that shown in the drawings. The other structural features of sheath assembly 11' and their intended functions are duplicated in this form of the invention and the same reference characters are used to identify similar elements. Of course, the inner and outer sheath members 31 and 29, respectively, would be of the appropriate lengths and diameters to accommodate the dimensions of the specific syringe assembly 12' with which it is associated. With such an arrangement, a clip 60 is employed to secure the mating flanges together. Clip 60 comprises a body portion 61 and a plurality of resiliently yieldable legs 62 extending from the four corners of the body portion 61 in a normal direction thereto with inturned prongs 63 disposed at the distal ends of legs 62. In attaching the clip 60, the legs 62 are manually spread apart outwardly to position the same over and about the flanges 58 and 59 and then released for snap-fitted engagement thereabout.

Figure 7:
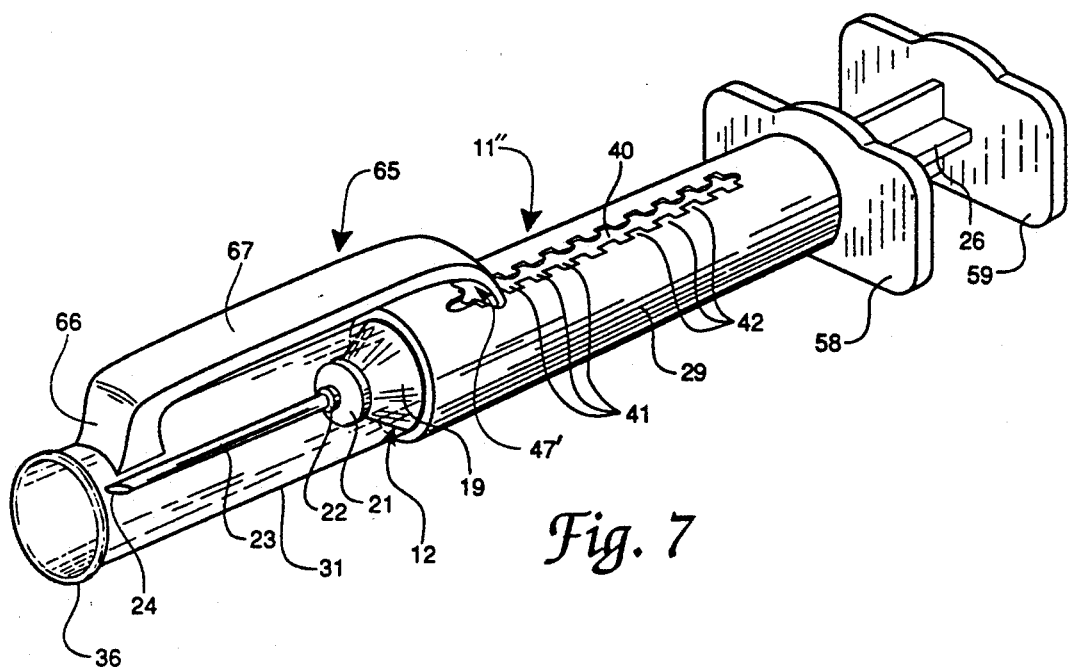
FIG. 7 is a perspective view of still another embodiment of the improved sheathed hypodermic syringe of the present invention.

FIG. 7 illustrates still another form of the present invention wherein the sheath assembly 11", comprised of inner and outer members 31 and 29, is similar in construction and operation to the sheath assembly first described in connection with FIGS. 1-4 except for the pawl which is modified in the form of an elongated clip, generally designated 65, of the type customarily mounted on mechanical pencils or pens. Clip 65 is provided with a base portion 66 welded or otherwise fixedly secured to the inner sheath member 31 adjacent the forward end thereof and an elongated bar 67 extending lengthwise of the inner sheath member 31. The bar 67 terminates in a pawl arrangement 47' similar in construction and operation to that depicted in FIG. 5. In the retracted position, the inner sheath member 31 would project forwardly beyond outer sheath member 29 to the extent dictated by the clip base portion 66 engagable with the shoulder 33 formed at the forward end of outer sheath member 29. Except for the clip 65 described above, the same reference characters are used to identify similar elements. The advantage of this form of sheathed hypodermic syringe is that the latter can be readily carried in the breast pocket of a health care provider.

From the foregoing, it is apparent that the objects of the invention have been fully accomplished. An improved sheathed hypodermic syringe is provided with novel actuating means to facilitate smooth and easy extension of the protective sheath over and past the needle point to preclude accidental needle stick to the user. The protective sheath is readily extended by a ratchet arrangement actuated by the fingers of the same hand holding the syringe, thereby allowing the surgeon, for example, to maintain his other hand on the patient. Thus, the surgeon can immediately extend the protective sheath over the needle after use without having to pass the exposed needle to an assistant or nurse further reducing the possibility of accidental puncture to the attendants.

It is to be understood that the forms of the invention herein shown and described are to be taken as illustrative embodiments only, and that various changes in the shape, size and arrangement of parts, may be resorted to without departing from the spirit of the invention.

I claim:

1. A sheathed syringe assembly comprising; a syringe assembly including a cylindrical body having an axially extending needle at one end thereof and a plunger slideably disposed in said body; a sheath assembly mounted on said body; said sheath assembly comprising inner and outer tubular members; said outer tubular member attached to said body at the other end thereof; said inner tubular member telescopically received in said outer tubular member and axially movable relative thereto between a retracted position exposing said needle and an extended position covering said needle; ratchet means operatively connected to said inner and outer tubular members for linearly advancing said inner tube member into said extended position; said ratchet means being manually operated by a user with the same hand holding said syringe assembly; said ratchet means including two parallel laterally spaced rows of axially spaced apart teeth formed in said outer tubular member and extending linearly therealong; and a pawl member affixed to said inner tubular member and slideable over said teeth to advance said inner tubular member.

2. A sheathed syringe assembly according to claim 1, wherein said pawl member is provided with a detent extending radially inwardly between axially spaced apart adjacent teeth and operatively coupled thereto whereby advancement of said pawl member toward said extended position causes said detent to continuously engage and slide over successive teeth permitting movement of said inner tubular member toward said extended position while movement in an opposite direction is prevented by engagement of said detent with said teeth.

3. A sheathed syringe assembly according to claim 1, wherein each tooth is provided with a substantially flat forward surface facing said one end of said body and an upper curved surface extending from the upper end of said forward surface and curving rearwardly and downwardly to an inner surface of said outer tubular member; said pawl member being provided with a detent extending radially inwardly between axially spaced apart adjacent teeth whereby advancement of said pawl member toward said extended position causes said detent to engage and slide over the curved surfaces of successive teeth permitting forward movement of said inner tubular member to said extended position while movement of said inner tubular member from said extended position rearwardly toward said retracted position is prevented by engagement of said detent with said flat forward surface of the preceding tooth.

4. A sheathed syringe assembly according to claim 1, wherein said laterally spaced rows of teeth define an elongated slot extending longitudinally of said outer tubular member; said pawl member including a base portion formed integral with said inner tubular member; a neck portion extending from said base portion and through said elongated slot; a transition portion extending from said neck portion and terminating in a lip overlying said outer tubular member, and a detent extending radially inwardly from said lip between axially spaced apart adjacent teeth of said laterally spaced rows of teeth.

5. A sheathed syringe assembly comprising; a syringe assembly including a cylindrical body having an axially extending needle at one end thereof and a plunger slideably disposed in said body; a sheath assembly mounted on said body; said sheath assembly comprising inner and outer tubular members; said outer tubular member attached to said body at the other end thereof; said inner tubular member telescopically received in said outer tubular member and axially movable relative thereto between a retracted position exposing said needle and an extended position covering said needle; ratchet means operatively connected to said inner and outer tubular members for linearly advancing said inner tube member into said extended position; ratchet means including two parallel laterally spaced rows of axially spaced apart teeth formed in said outer tubular member and extending linearly therealong; and a pawl member affixed to said inner tubular member and slideable over said teeth to advance said inner tubular member.

6. A sheathed syringe assembly according to claim 5, wherein said pawl member is provided with a detent extending radially inwardly between axially spaced apart adjacent teeth and operatively coupled thereto whereby advancement of said pawl member toward said extended position causes said detent to continuously engage and slide over successive teeth permitting movement of said inner tubular member toward said extended position while movement in an opposite direction is prevented by engagement of said detent with said teeth.

7. A sheathed syringe assembly according to claim 5, wherein each tooth is provided with a substantially flat forward surface facing said one end of said body and an upper curved surface extending from the upper end of said forward surface and curving rearwardly and downwardly to an inner surface of said outer tubular member; said pawl member being provided with a detent extending radially inwardly between axially spaced apart adjacent teeth whereby advancement of said pawl member toward said extended position causes said detent to engage and slide over the curved surfaces of successive teeth permitting forward movement of said inner tubular member to said extended position while movement of said inner tubular member from said extended position rearwardly toward said retracted position is prevented by engagement of said detent with said flat forward surface of the preceding tooth.

8. A sheathed syringe assembly according to claim 5, wherein said laterally spaced rows of teeth define an elongated slot extending longitudinally of said outer tubular member; said pawl member including a base portion formed integral with said inner tubular member, a neck portion extending from said base portion and through said elongated slot, a transition portion extending from said neck portion and terminating in a lip overlying said outer tubular member; and a detent extending radially inwardly from said lip between axially spaced apart adjacent teeth of said laterally spaced rows of teeth.

* * * * *